(12) United States Patent
Austen et al.

(10) Patent No.: US 6,564,655 B1
(45) Date of Patent: May 20, 2003

(54) ANALYTICAL SAMPLING DEVICE

(75) Inventors: Malcolm Trayton Austen, Middlesex (GB); John Robert Dodgson, Surrey (GB); Monica Backes, Ealing (GB); David Wenn, Middlesex (GB); Richard Lynn Hedgeley, Middlesex (GB); Mark Seymour, Berks (GB)

(73) Assignee: Central Research Laboratories Limited, Middlesex (GB)

( * ) Notice: Subject to any disclaimer, the term of this patent is extended or adjusted under 35 U.S.C. 154(b) by 0 days.

(21) Appl. No.: 10/031,191
(22) PCT Filed: Jul. 14, 2000
(86) PCT No.: PCT/GB00/02716
§ 371 (c)(1),
(2), (4) Date: Jul. 5, 2002
(87) PCT Pub. No.: WO01/06229
PCT Pub. Date: Jan. 25, 2001

(30) Foreign Application Priority Data

Jul. 15, 1999 (GB) .............................................. 9916649

(51) Int. Cl.⁷ ............................................. G01N 35/10
(52) U.S. Cl. ................... 73/863.02; 73/863.01
(58) Field of Search ......................... 73/863.02, 863.01, 73/863.21, 61.59; 422/81

(56) References Cited

U.S. PATENT DOCUMENTS

| 4,798,095 A | * | 1/1989 | Itoh | 73/863.01 |
| 5,301,261 A | * | 4/1994 | Poole et al. | 395/82 |
| 5,303,598 A | * | 4/1994 | Binder et al. | 73/863.01 |
| 5,512,168 A | * | 4/1996 | Fetner et al. | 210/198.02 |
| 5,660,792 A | * | 8/1997 | Koike | 422/63 |
| 5,844,147 A | * | 12/1998 | Fiedler et al. | 73/863.21 |

FOREIGN PATENT DOCUMENTS

| GB | 2352035 A | * | 1/2001 | G01N/1/14 |

OTHER PUBLICATIONS

Astle, US patent application US 20020084214A1, Jul. 4, 2002.*

* cited by examiner

Primary Examiner—Daniel S. Larkin
Assistant Examiner—C D Garber
(74) Attorney, Agent, or Firm—Martin Fleit; Paul D. Bianco; Fleit Kain Gibbons Gutman & Bonjini F.L.

(57) ABSTRACT

Apparatus for sampling a liquid, said apparatus comprising:
  i) a sampling device capable of automatically taking a known volume of liquid from a source;
  ii) fixing means connected to said sampling device and removably attachable to a solid phase extraction (SPE) unit, the fixing means being arranged such that liquid taken from a sample by the sampling device is passed directly through the solid phase extraction unit;
  iii) a reading device able to read labels on an SPE unit attached to said fixing means;
  iv) a controller arranged to log codes based upon a signal from the reading device, and thereafter issue instructions to an operator and/or operate the sampling device to take an appropriate volume of liquid in response to a signal from said reading device.

Methods of sampling using the apparatus are also claimed. These are useful in, for example analysis methods.

15 Claims, 6 Drawing Sheets

ANALYTICAL SAMPLING DEVICE

FIELD OF THE INVENTION

The present invention relates to apparatus for the automatic sampling of liquids, in particular for use in field conditions, where samples of accurate volume are to be taken for example for analysis. In addition, the invention includes methods of sampling and sample preparation using said apparatus.

BACKGROUND OF THE INVENTION

During many environmental monitoring procedures, samples of water such as groundwater are extracted and stored for subsequent laboratory analysis. At present this is mainly done manually, though a variety of devices exist to assist the process. In order to prevent changes in composition through e.g. bacterial activity, samples may have to be stored and transported frozen, which results in significant cost. Once in the laboratory, organic residues are extracted from the sample by passing the sample through a solid phase extraction (SPE) unit. Residues are then eluted from the unit into a smaller volume and analysed by for instance chromatography (gas or liquid) and/or mass spectrometry. Considerable cost and effort can be saved if the SPE stage could be carried out at the time of sampling.

The basic process of SPE in field conditions is well known and devices such as simple syringes have been used for many years. A typical process might involve the following steps:

(i) attaching an SPE unit to a syringe;
(ii) placing a sample in a container, such as a disposable cup;
(iii) drawing an accurate volume of the sample through the unit; and
(iv) recording sample details and marking the unit accordingly.

The operation of such a process is manual, and often requires dexterity in manipulating simultaneously a sample cup, a syringe and a unit which may be difficult under adverse conditions (bad weather, or operation in a boat at sea for example). Furthermore, a number of discrete operations are required, each of which might fail or be subject to error. In particular, the sample volume must be known to +/−1.5% or better, and blockage of the unit before the full syringe volume is filled, or presence of bubbles in the syringe, will compromise this. Alternatively the sample might be measured into the cup, or the volume drawn through might be measured, but this will be difficult and time consuming under adverse field conditions. Furthermore, the details of the sample need to be recorded manually, and they again might be difficult or subject to error.

Devices which offer multi-function or multi-channel options, which are often automated, are known in the art. For instance, U.S. Pat. No. 5,167,802 describes a field-use autosampler which takes samples through a nozzle and directs them through a multi-way valve to an SPE cartridge, then into a vessel for volume readings. This is suitable for stand alone use but requires complex valving, has common sampling lines and plumbing upstream of the SPE cartridge. This means that cross-contamination is likely unless complex and time and sample consuming wash processes are used. In some situations however, the amount of sample available is limited and so these wash steps may not be possible.

U.S. Pat. No. 5,844,147 describes a method of field sampling in which the sample is drawn rapidly, stored under pressure and then passed through an SPE cartridge. This does not address the requirement for easier data handling in the field which a semi-automated device with accurate sample volume determination can give.

A simpler device, designed to be operated easily but with greater security of information and less scope for error, is required.

SUMMARY OF THE INVENTION

The present invention provides apparatus for sampling a liquid, said apparatus comprising:

i) a sampling device capable of automatically taking a known volume of liquid from a source;
ii) fixing means connected to said sampling device and removably attachable to a solid phase extraction (SPE) unit, the fixing means being arranged such that liquid taken from a sample by the sampling device is passed directly through the solid phase extraction unit
iii) a reading device able to read labels on an SPE unit attached to said fixing means;
iv) a controller arranged to log codes based upon a signal from the reading device, and thereafter issue instructions to an operator and/or operate the sampling device to take an appropriate volume of liquid in response to a signal from said reading device.

The apparatus of the invention allows sampling to be undertaken in a simple, one-handed operation in which the sample is metered. The possibility of errors arising in this operation is low.

The SPE unit employed in the apparatus of the invention may be in any of the known forms, including cartridges and discs. The pump is arranged to draw liquid directly through the SPE unit which means that the sample encounters the unit before any other part of the apparatus.

Suitably the fixing means allows firm fixing of an SPE unit to an end portion of the sampling device. They may for example, comprise a series of interconnectable elements, some of which are provided in the sampling device and other of which are provided around the top of the SPE unit such as the cartridge. These elements may take various forms including locking and sealing elements as are well known in the art. In particular, however, they comprise a female Luer fitting which is in the form of a "pistol grip" which interconnects with the male Luer fitting on the SPE unit. In this arrangement, the walls of the pistol grip are arranged to fit closely around the barrel of an SPE cartridge. A sealed fixed interconnection can be established by pushing the cartridge into the pistol grip and twisting it slightly.

Preferably, the apparatus of the invention forms part of a system which further comprises one or more SPE units, each of which carries a machine readable label, in particular a unique label which is readable by the reading device of the apparatus. Examples of such reading devices are barcode readers so that each SPE unit carries a barcode, preferably a unique barcode, which may be printed or embossed onto the surface.

A controller is able to log the label or code of each SPE unit which is fitted into the apparatus. Preferably, the controller includes an interlock means which inhibits the sampling device from operating unless an appropriate code has been read by the reader. Where barcodes (or other labels) are unique to each SPE unit this will preclude the possibility of the same SPE unit being used on more than one occasion in error.

Once the controller has recognised that an appropriate unused SPE unit is in position, it may issue instructions to an operator, for example by way of a display device. These instructions may include directions for setting the sampling device so that the correct volume of sample is drawn, or for starting the operation of the sampling device.

Suitably interlock means are also provided and set to prevent the operation of the sampling device unless any instructions issued by the controller have been correctly implemented by the operator.

Alternatively, or additionally, the operation of the sampling device is effected automatically by the controller once the SPE unit is in place and any instructions issued by the controller to the operator have been correctly implemented.

The controller suitably monitors the progress of the sampling device and stores this data automatically, so that the conditions under which each individual SPE device have been treated are recorded.

Suitably the apparatus further comprises a data input device such as a keyboard or buttons, which allows the operator to manually input data for instance, to record if it becomes necessary to 'void' a sample, and optionally also to record the reasons for this.

The sampling device is suitably one which uses vacuum or pump action to draw an accurately known volume of liquid. Such devices are known in the art and may include pistons or syringes having a fixed volume, which are used to draw up a known volume of liquid (see for example U.S. Pat. No. 3,607,092). Working on a broadly similar principle, tube devices such as those described in U.S. Pat. No. 4,987,785, have been proposed in which liquid is caused to flow into a section of tubing having a predetermined volume. Other devices use ballcocks or ball valves (see for example U. S. Pat. No. 4,083,2520, U.S. Pat. No. 4,077,263). In the former devices, liquid flows into a vessel until a fixed level is reached, whereat a ballcock floats up and causes the flow to stop. Ballvalve devices are similar except that the ball is arranged directly below the liquid inlet such that at a fixed level the ball floats up and stoppers the inlet. Also known are timed pumps (e.g. U.S. Pat. No. 4,121,907) where a pump acts for a fixed time, so moving a fixed volume of liquid.

A particularly preferred sampling device, which provides for particularly accurate volume measurement without errors caused by gas bubbles is described in the Applicant's copending Patent Application of even date entitled "Method and Apparatus for Taking Liquid Samples of Known Volume" (published as International Publication No. WO 01/06229 A2. This device comprises a vessel of known volume, the vessel comprising a chamber having an inlet to allow liquid to enter said chamber, wherein at least a portion of a surface of the chamber is formed of a gas permeable membrane, and said portion is arranged such that gas bubbles present in the chamber will exit through said membrane.

The total volume of the vessel comprises the volume of the chamber combined with that of the relevant parts of any conduits leading to or from the chamber, and this can be accurately set prior to sampling.

The membrane is arranged such that at least some of it is in contact with any head space formed by gas bubbles in the liquid, so as to allow any gas to exit from the chamber. Thus any gas bubbles that are present in the liquid prior to or during the sampling operation are removed and hence do not compromise the volume measurement accuracy.

Preferably, the gas permeable membrane is arranged in an upper surface of the chamber as any gas bubbles present in the liquid in the chamber will rise up through the liquid and so will contact across the entire surface of the membrane thus maximizing efficiency. However, the membrane may be present elsewhere, for example in the side wall of the chamber provided gas bubbles may be drawn through it.

In a preferred form of the sampling device, walls of the chamber include a region which tapers inwardly towards the membrane since gas bubbles will tend then to be channelled towards the membrane as they rise through the liquid. Such a chamber is preferably held substantially vertically but a chamber having walls that taper at an angle of x° to its axis will be able to tilt to an angle of (90-x)° and without trapping gas in any "pockets" formed by the taper (see FIG. 2b below).

The inlet is suitably arranged at an upper portion of the chamber. Suitably the chamber contains a separate outlet for the liquid. This is preferably arranged at a lower portion of the chamber to allow for gravity drainage if required. Alternatively a pump may be provided to remove liquid from the chamber after use.

Suitable gas permeable liquid impermeable membranes are known in the art. They include polytetrafluoroethylene (PTFE) membranes such as those available from Mupor Ltd., UK. They may be held in place in the chamber by fixing means such as flanges, screws and the like, or where the materials of the membrane and the remainder of the chamber allow, they may be attached to the surrounding chamber walls for example by heat or ultrasonic sealing.

Where necessary, support means can be provided for the membrane. These may take the form of a mesh or grid, for example of a rigid material such as metal or plastics, which holds the membrane to prevent distortion but allows gas to pass through. Alternatively, the membrane may be provided with an annular support that allows gas to pass through the central region. Preferably also in this arrangement, the membrane extends outwardly around the support, so increasing the available membrane surface.

For automatic operation, the sampling device further comprises a pump for pumping liquid into the vessel. A suitable pump is a vacuum pump which is arranged to draw liquid into the vessel, for example by inducing a reduced pressure or vacuum in the chamber. In such an arrangement, the membrane is suitably arranged to form a barrier between the chamber and the vacuum pump. A convenient location for the membrane in this instance is across the vacuum line leading from the body of the chamber to the vacuum pump. In this case, gas present in the chamber is drawn out through the membrane by the pump.

The membrane may be held in place in a vacuum line for example by means of a flange arrangement provided specifically for the purpose.

Alternatively, the pump comprises a positive pump which is arranged to drive sample liquid into the vessel.

In a particularly preferred embodiment, the sampling device is provided with means for halting the pump when the vessel is full. This may comprise a sensor device, which is operatively interconnected with a controller for the pump. Suitable sensors include a pressure sensor or a level sensor, or a combination of one or more of these. For example, where liquid is drawn into the vessel by means of a vacuum pump through the gas permeable membrane, the pressure in the vacuum line will drop significantly when the vessel is full and all gas bubbles have been drawn out. Thus a pressure sensor arranged in the vacuum line would detect this pressure change which would result in a signal being passed to the controller which would halt the vacuum pump. Conversely, where the sampling device comprises a pump arranged to drive liquid into the vessel, the pressure in the vessel would increase significantly when the chamber is full, and a pressure sensor in the feed line would detect this change.

Level sensors, for example optical devices, might be used to detect when liquid reaches exactly the level of the top of the vessel. It is difficult to ensure the accuracy of the position of such a sensor however, and so pressure sensors may be preferred in this context. However, in a particular form of the sampling device, a level sensor is provided in addition to the pressure sensor, and is arranged to detect a 'nearly full' condition of the chamber. A controller can then be arranged to slow the pump in response to a signal from the level sensor. This will reduce the pressure shock to the upper surface of the chamber, which may contain the membrane, when the liquid reaches it.

If required, the volume of a chamber (and thus the vessel) may be adjustable. For example, a wall of the chamber may be of a flexible material which is deformable under the influence of an externally applied pressure, so as to alter the volume in the chamber. In this case, suitable means for applying the deforming pressure, such as a piston or a screw, is provided externally of the chamber. These devices are suitably driven electronically so as to ensure that accurate deformation occurs.

Alternatively, the volume of the vessel may be adjusted by providing a piston or plunger with a seal in the chamber. In yet another embodiment, the gas permeable membrane is moveable, for example by attaching it to the end of a probe which can move up and down within the chamber. In this way the height of the liquid in the chamber, and hence the volume, can be selected prior to taking a sample.

The adjustment of the volume of the vessel is effected in a measurable way. This provides for greater flexibility of use of the apparatus, in particular where there are situations where the supply or source of liquid is low and there may not be sufficient available to fill the vessel. In this case, a volume such as the available volume of liquid may be pumped into the vessel and afterwards, the volume of the vessel may be adjusted until the volume of liquid completely fills the vessel. Further pumping will ensure that any air bubbles are removed as described above. At this point, the actual volume of liquid will be the volume of the vessel.

Suitably, a further component of the system comprising the apparatus of the invention is a storage box for the SPE units which protects them from contamination before and after use, SPE units might be preconditioned if necessary in a laboratory before being loaded into the box. In use, the units are suitably removed from the box one at a time as needed, and used units returned to the box. The box preferably has twice as many locations as units initially so that used units can be placed back into the same box from which they were drawn but in a separate section of the box, to ease tracking of the units throughout the process.

The system may further include a data recording or storage means such as a printed record, magnetic storage stripe or an electronic storage device such as an 'ibutton' (TM of Dallas Semiconductor, US) so that data about preconditioning and relevant sampling process(es) might be stored together with the used units. This is suitably provided in the SPE storage box and is interconnected with and responsive to data provided by the controller.

Optionally a printer which records sample data on the used SPE units or a sealed wrapper or container placed around them is also provided.

Suitably the storage box is in the form of a cassette which presents units and in particular SPE cartridges for attachment to the sampling device one at a time.

Preferably, the SPE units are sealable in the storage box. This may be achieved by means of a bung onto which SPE cartridges are placed, and a series of flanges appropriately positioned on the floor of the box so as to interlock with corresponding wings, provided on the rim of the cartridge if appropriately designed.

Presentation of cartridges from the box may also be under the command of the controller so as to ensure that only the correct cartridge is presented to the user. The acceptance of used SPE cartridges back into the box may also be under command of the controller. This provides additional security that cartridges are used only once, and/or that preconditioned cartridges are used in an appropriate predetermined order. Suitably therefore the box is "smart" and presents the user with an appropriate cartridge for use and then presents the user with a suitable empty space in which to place the used cartridge. A particularly suitable type of box for this will have a carousel arrangement for storing cartridges.

Suitably, the box is designed such that units contained within it are sealed to prevent contamination. For unused units, this may be achieved for example by providing a sealing film over the units once they are in place in the box. Suitably, the fixing means is adapted to rupture the seal during a unit collection operation so that the risk of contamination is minimised. A pistol grip type fixing means as described above is particularly suitable for such an operation.

The lid of the box, in particular in the section set aside for used SPE units may be provided with detachable sealing means, arranged such that when the lid of the box is closed, the sealing means engage with any used SPE units present and seal them to prevent contamination. If the lid is raised again, the sealing means become detached from the lid and remain in place on the unit. The sealing means may be adapted to fit the particular SPE units being used but may include bungs and Luer caps.

Suitably geographical locations from which the samples are taken are also coded and a reader, which may be the same reader as used in the apparatus described above, is used to record this and signal the controller. This means that in use, an operator has to go to a particular location, read in the code at that location, attach a correctly coded SPE cartridge, and only then will the controller allow a sample to be taken. An advantage of this is that the location of a site from where a sample is taken is known and there is a permanent record of the site location on the sample.

This sample code might be physically associated with a sample location, e.g. a barcode mounted on a sample well. Alternatively, a location may be determined using, a Global Positioning System (GPS) receiver which is operatively interconnected or integral with the controller.

In a particularly preferred embodiment, the controller is provided with a programme which allows experimental protocols written in, for example a spreadsheet programme, to be translated into a sequence of instructions to the operator, and then relating these to data inputs from the code reader and/or any input device to confirm that a correct sequence has been performed. The programme would then associate each used SPE unit with a particular sample.

The invention further provides a method of sampling a liquid, using apparatus as described above, said method comprising
  i) fitting a SPE unit having a machine readable label thereon, to the fixing means of said apparatus;
  ii) reading the label on said SPE unit using a reading device which signals a controller with label information;

iii) placing an inlet of said SPE unit into a source of sample liquid; and iv) carrying out any instructions issued by the controller so as to cause activation of the sampling device.

Prior to use, the controller is suitably programmed with the desired sample protocol in a laboratory. The SPE units, in particular SPE cartridges, which are pre-labelled for example with a unique barcode, are preconditioned in the laboratory as required, and suitably then placed and preferably interlocked into a storage box as described above. The data about their preconditioning, if required, is suitably downloaded to a memory device in the box. The experimental protocol is also downloaded to the controller either prior to field use or even during field use, if the controller is linked to a base computer.

In the field, an operator would take the apparatus to the first sample location and, where available, enter the code from that location into the controller for example, using the barcode reader on the device or via a GPS receiver (not shown).

The storage device may then offer up an appropriate SPE unit or this may be selected manually. The SPE unit is then attached to the sampling device, and the unit code read using the reader. The controller checks the protocol, checks that the unit has not been used before and has the correct preconditioning, then releases the interlock, where present, allowing removal of the unit from the storage box.

The operator if necessary, then takes a sample into a container such as a disposable cup and inserts the inlet of the SPE unit into the sample. Alternatively, the inlet of the SPE unit can be applied directly into the sample source, such as the river, stream, well, groundwater source or the sea. Activation of the trigger or button, for instance in response to the instructions displayed by the controller, will start the sampling process.

The sampling device(which suitably includes a vacuum pump), then draws the correct volume of sample liquid through the unit and confirms to the controller that this has happened. In this method, the volume of the vessel may be predetermined and liquid is caused to enter the vessel until it is completely filled. Alternatively, where the apparatus has a chamber of adjustable volume, a volume of liquid insufficient to fill the vessel is pumped in and the volume of the vessel is then adjusted so that that the liquid completely fills the vessel in the absence of gas bubbles. The volume of the vessel in this configuration is then recorded and so provides an accurate measure of the actual volume of liquid in the sample.

On completion of the sampling operation, the operator replaces the unit into the 'used' section of the box and detaches it from the holder. Where the SPE unit is a cartridge, the used cartridge is preferably sealed in order to prevent cross-contamination, either by capping it manually or by using an automatic capping system incorporated into the lid of the box.

BRIEF DESCRIPTION OF THE DRAWINGS

The invention will now be particularly described by way of example with reference to the accompanying diagrammatic drawings in which.

DETAILED DESCRIPTION OF THE EMBODIMENTS

Figure 1:
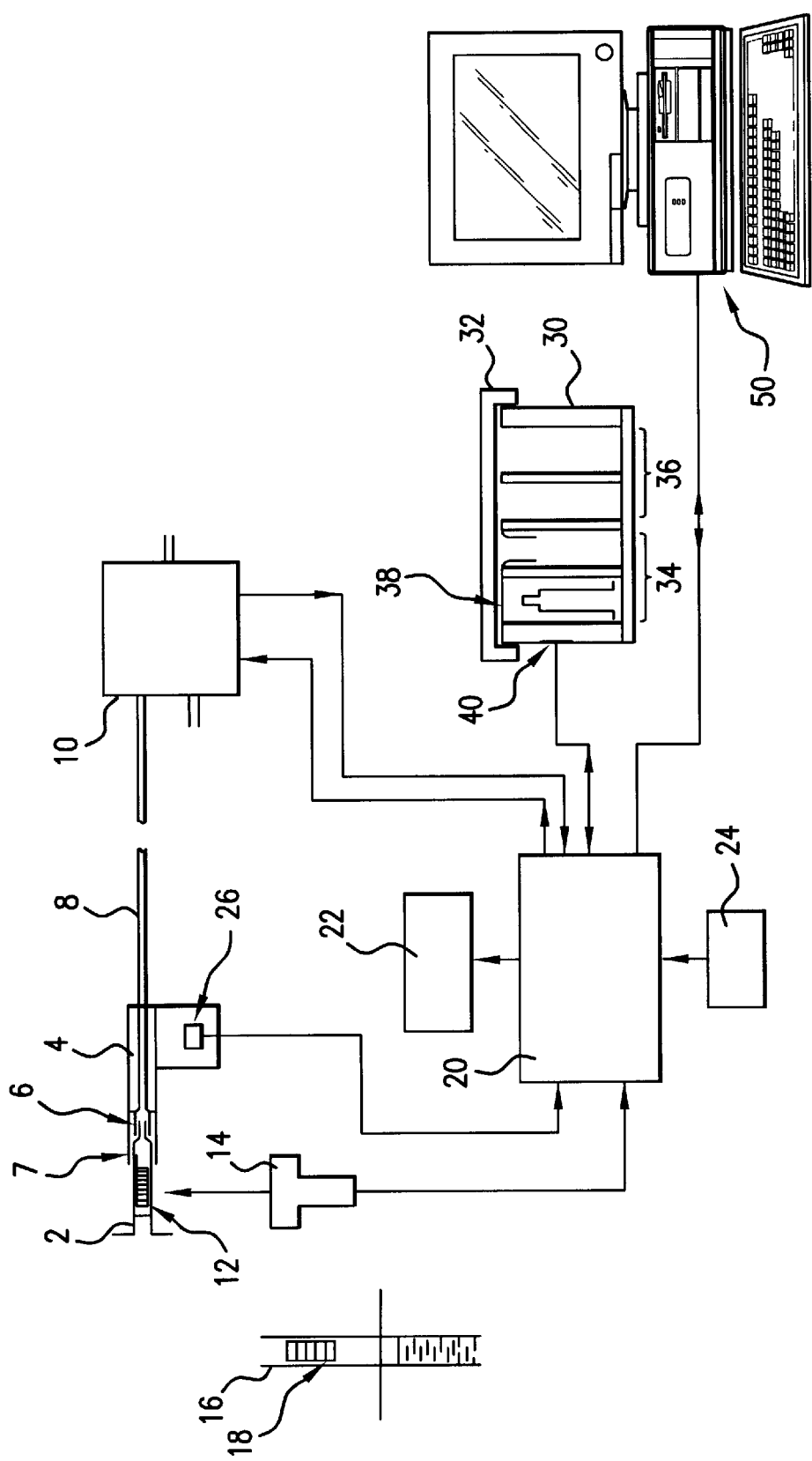
FIG. 1 is a diagram showing a system of the invention for use in a field situation.

In the illustrated apparatus (FIG. 1), an SPE cartridge 2 is removably attached to a holder 4 by means of a Luer fitting 6. The holder 4 is conveniently in the form of a 'pistol grip'. A portion 7 of the holder extends around the tubular part of the SPE cartridge in order to prevent flexing of the cartridge breaking the Luer connection. Portion 7 might be a close fit to the cartridge 2 but it is intended that the main part of the frictional force providing connection is in the Luer fitting.

The pistol grip 4 is connected via sample tube 8 to a sampling device which includes a pump unit 10 (details in FIG. 2, described below). The SPE cartridge 2 is provided with a unique code 12, e.g. a printed or embossed bar code. A code 18 is also provided on the sample well 16.

A bar code reader 14 able to read the codes 12, 18 is provided and is connected to a controller 20 so as to pass a code signal to it. The controller 20 includes a display device 22 which can show instructions stored in the controller's memory for use by an operator. An input device 24 comprising a keyboard or buttons is also provided so as to allow an operator to enter data manually into the controller 20.

The controller 20 is connected to the pump unit 10 so that it can activate operation of the unit on receipt of the activating signal which can be generated by manual operation of button 26, and thereafter monitor operation of the pump unit 10. It is further connected to a data storage device 40 which is attached in this case, to a cartridge storage box 30. The box includes an area 34 for storage of unused cartridges, and a separate area 36 intended for storage of used cartridges. Each cartridge holder in the area 34 is sealed prior to use with a plastic film 38, which may be metallised, and the entire box 30 is coverable with a lid 32.

The controller 20 is further connected to a computer 50 which may be remotely located, for example in the base workstation.

In use the holder 4 engages an unused cartridge 2 in the box 30. The holder 4 is designed to automatically rupture the seal 38 in the process of engaging a cartridge 2. The bar code reader 14 reads the code 12 on the cartridge and optionally a code 18 on the sample well 16 and passes these codes to the controller 20. The controller 20 processes this data and provides instructions to the operator from its memory via display 22. If necessary, the operator can input code information to the controller 20 via keyboard or input buttons 24.

When the codes have been recorded and checked, and the input of the cartridge 2 is placed in contact with sample liquid, for example in a container such as a disposable cup, the operator presses button 26 which causes the controller to initiate the sampling cycle. The controller 20 monitors outputs from sensors in the pump unit 10 and verifies that the correct sample volume has been taken. If the sample volume is too small, the controller 20 informs the operator who can then measure the actual volume sampled when it is drained. A control button is provided on input unit 24 to allow the operator to void the sample. If required the reasons for this can be input also by the operator using unit 24.

When the sampling process is complete, checked data is transferred to the data storage device 40 attached to the cartridge carrier box 30. The device 40 might be for example a printed record on the box, a magnetic strip, or an electronic memory device.

The storage box 30 is designed to store SPE cartridges which have, if necessary, been preconditioned prior to going into the field, and to protect used cartridges. The lid 32 prevents contamination and optionally has associated with it means for automatically capping the used cartridges (see FIG. 3).

Unused cartridges are stored in compartments sealed with e.g. a plastic film 38 which is designed to be ruptured by the pistol grip 4 when this is inserted into the compartment to extract a cartridge. The end tube 7 of the pistol grip guides the cartridge such that the Luer fittings 6 engage.

Used cartridges are stored (after optionally drying the outside with a blower (not shown)) in an area 36 of the same box, separate from the area 34 for unused cartridges. Data regarding the preconditioning process and the treatment to which the cartridges have been subjected is suitably stored together in the data storage device 40 on the box 30.

Finally data is ported to the computer 50 back at the base station from the controller 20. Data links may be provided to allow the computer 50 to devise experimental protocols and download these to the controller 20, so that 20 can give sequential instructions to the operator if required.

Figure 2:
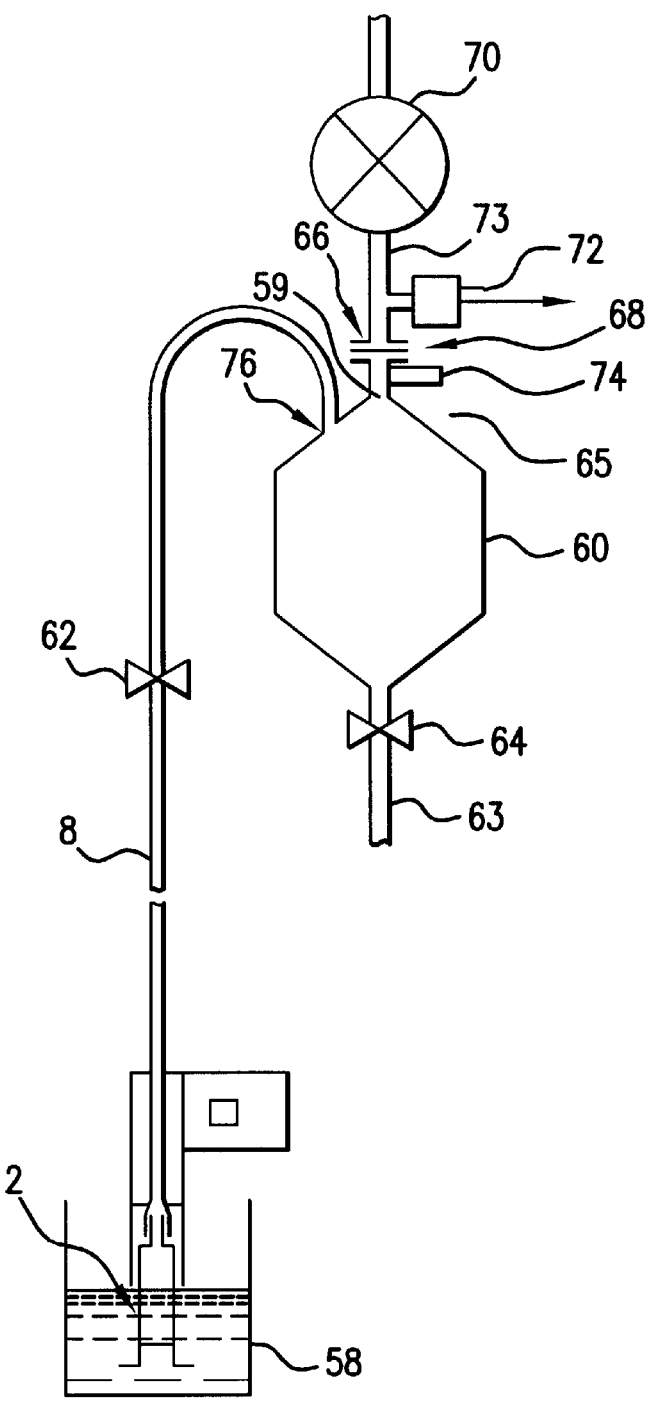
FIG. 2 shows an embodiment of the sampling device used in the apparatus of the invention attached to an SPE cartridge.
Figure 2A:
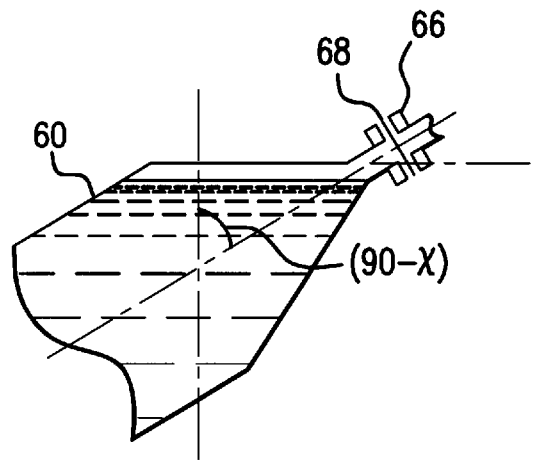
FIGS. 2a–2d illustrate modified forms of a component of this device.
Figure 2B:
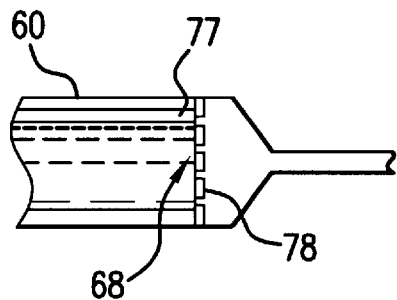
Figure 2C:
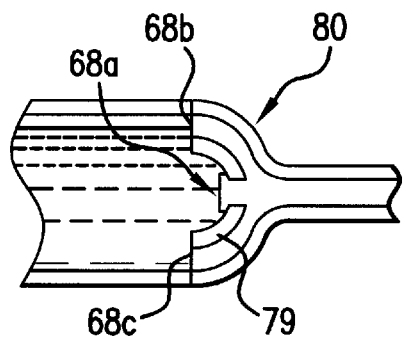
Figure 2D:
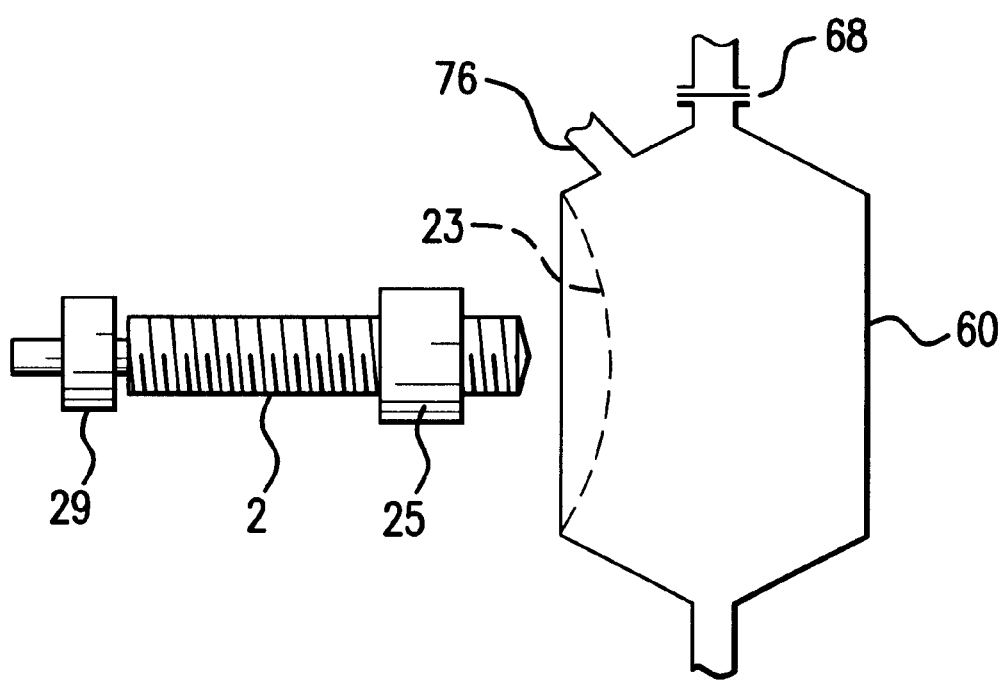

A preferred form of the sampling device (of which the pump unit 10 forms a part) is illustrated in FIG. 2. In this device, a sample tube 8 is connected to a chamber 60 via an inlet port 76 by way of an inlet valve 62. A drain channel 63 is connected to the chamber 60 by way of a drain valve 64. The drain channel 63 is connected at a lower region of the chamber 60 so as to allow for gravity drainage, although a pump may be provided to allow for forced drainage.

The chamber 60 has a tapering top portion 65 and an opening 59 at the top which is connected to a pump 70 by way of a pumping line 73. A gas permeable, liquid impermeable membrane 68 such as a PTFE membrane, is held across the pumping line 73 by means of a clamped flange arrangement 66.

A pressure sensor 72 is provided in the pumping line 72 and a level sensor 74 is arranged in the line intermediate the opening 59 and the membrane 68.

In use, the pump 70 operates to evacuate the chamber 60 and so draw in liquid from a reservoir 58 first via the cartridge 2, and then tube 8 and valve 62. Alternatively, the inlet of the cartridge may be placed directly into the sample source, such as the sea, a river or well. Air from above the liquid level is evacuated until the chamber 60 is full. When the liquid reaches the membrane 68, it is unable to pass through it, and the pump 70 then runs to remove any residual bubbles in the system. The pressure in the pumping line will then fall suddenly and this is detected by the pressure sensor 72, which is monitored by the controller 20. The level sensor 74 is arranged to detect a 'nearly full' condition, whereupon the controller 20 is programmed to slow the pump, in order to reduce pressure shock to the membrane when the liquid reaches it.

The pattern of response of the pressure and optionally the level sensor can be checked by the controller 20 to determine that the correct sample volume has been drawn.

Correct operation is expected to give a gradually falling pressure while air is being pumped and liquid drawn up the tube 8—the precise profile will depend on the head of liquid and how this changes with time—but with a sudden drop when the liquid reaches the membrane. Algorithms are provided in the controller to distinguish between correct and incorrect filling patterns.

In the illustrated embodiment, the volume of sample liquid is drawn from a reservoir 58 through an SPE cartridge 2. It is clear then that the total volume of the liquid drawn through the absorbent bed of the cartridge 2 (and thus the total volume of the vessel in this case) is the total of the volume of the cartridge 2 above the absorbent bed, tube 8, chamber 60 and the pumping line 73 up to the membrane 68.

The rate of drawing of sample through the cartridge can be set by the rate of the pump, or by an air bleed inserted into the pump line (not shown). Constant rate is not normally required but can be stabilised by e.g. using a large bleed and fast pump, or a significant pressure drop in the pump line such that the additional effect of changing head of water is negligible, or by active feedback control of the bleed or pump speed.

Once the sample volume has been drawn, it is necessary to empty the vessel. This is accomplished by closing inlet valve 62 and opening drain valve 64. Drainage might be forced by reversing the pump, or providing a separate drain pump (not shown). The inlet port 76 is arranged near (or preferably at) the top of the chamber 60, so that liquid is between the port 76 and the membrane 68 for as little time in the filling cycle as possible. This will ease identification of correct filling using pressure sensing.

Alternative designs of pumping unit might be used. For instance, a liquid pump might be located in tube 8, using positive pressure to fill the vessel and expel air through the membrane 68. Two pumps might be used if necessary or desired.

In the illustrated embodiment, the chamber 60 as well as the entire sampling vessel system is kept vertical by mounting it on a gimbal arrangement (not shown).

The apparatus may be modified to allow for operation in a wider range of orientations, provided only that the vessel contains no areas in which gas pockets could become trapped and fail to reach the membrane 68. For example, a chamber 60 with walls that taper at an angle of x degrees to its axis will not trap gas, even if tilted up to an angle of 90-x degrees from the vertical(FIG. 2$a$).In this embodiment, x will typically be from 5 to 80, in particular from 30 to 50.

If a greater inclination is required, a larger membrane 68, extending over an entire end of the chamber 60 may be provided (FIG. 2$b$). In this case, any gas bubbles in the chamber 2 will rise to the top of the chamber to form a head space 77. The pump (not shown) acting to force gas in the direction of the arrow will continue to act provided the head space contacts the membrane 68. In this case a case a support mesh 78 is provided to prevent distortion of the membrane.

In an alternative arrangement (FIG. 2$c$), the membrane is supported by means of an annular support 79, held within a correspondingly shaped end region 80 of the chamber 60. In this case, the available area of membrane for gas escape comprises a central region 68$a$ and a circumferentially arranged areas 68$b$, 68$c$.

In the embodiment illustrated in FIG. 2$d$, a side wall 23 of the chamber 60 is flexible, allowing adjustment or calibration of the sample volume by means of an actuator 25 in contact with the side wall 23. This actuator 25 may be under the control of the controller 20 such that the volume of the chamber at any time is known.

The internal volume of the chamber may be adjusted by the screw 27 of the actuator 25 which are driven by a motor 29. Using suitable encoding means (not shown) on the screw, the position of the screw 27 and hence volume of the chamber 60 can be accurately determined. The volume of the chamber 60 is adjusted prior to or after taking a sample. A sample of the required volume can then be drawn into the vessel as described above.

Figure 3:
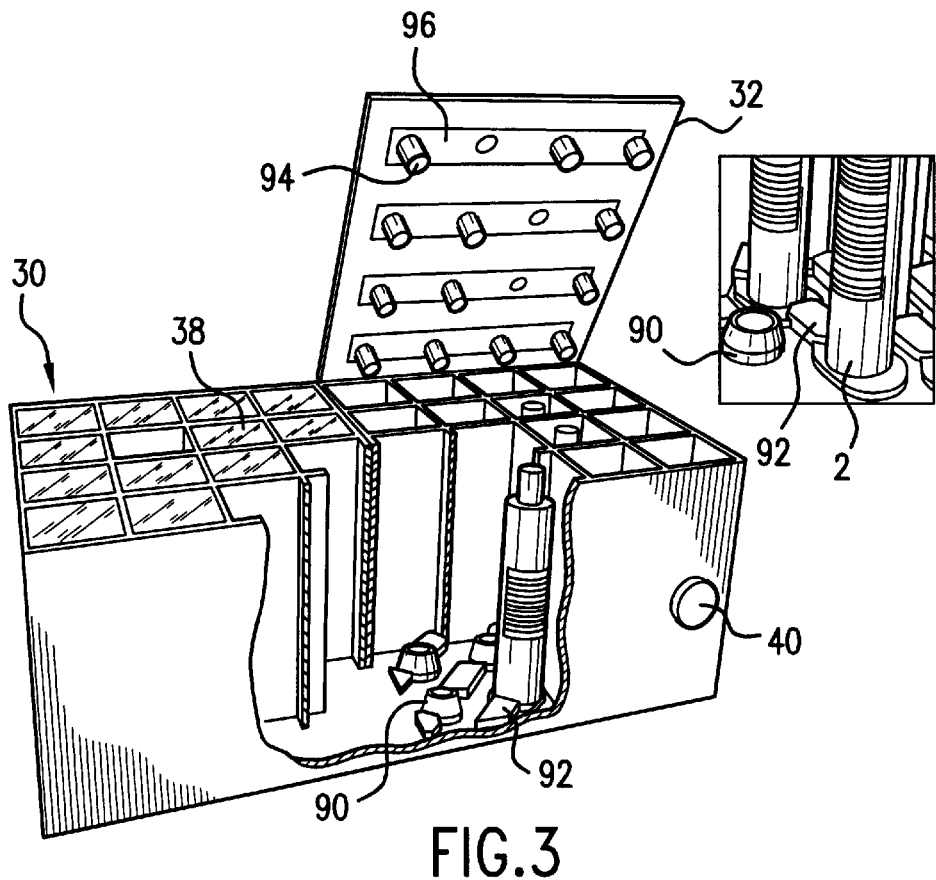
FIG. 3 illustrates a SPE cartridge storage box useful in conjunction with the apparatus of the invention.

FIG. 3 shows in detail an embodiment of the storage box 30. Unused cartridges are shown on the left sealed under film 38. Used cartridges are on the right. The pistol grip is able to push cartridges onto sealing bungs 90, which form a close fit but allow rotation. Rotation using the pistol grip rotates the cartridges until the flanges on the cartridges lock under a mechanism 92 made up of a set of overhanging flanges. This then holds the cartridge while the Luer coupling is released, e.g. by further rotation of the pistol grip.

The lid 32 has Luer caps 94 attached to it by an adhesive film 96, such that when the lid is closed the caps engage on the Luer coupling on any cartridges present and seals them. Upon raising lid 32, the Luer caps 94 are removed from the adhesive film 96 and retained on the cartridges. The Luer caps 94 and sealing bungs 90 act to seal both ends of the cartridges and thus prevent any egress of liquid from the cartridges which may cause cross contamination.

Figure 4:
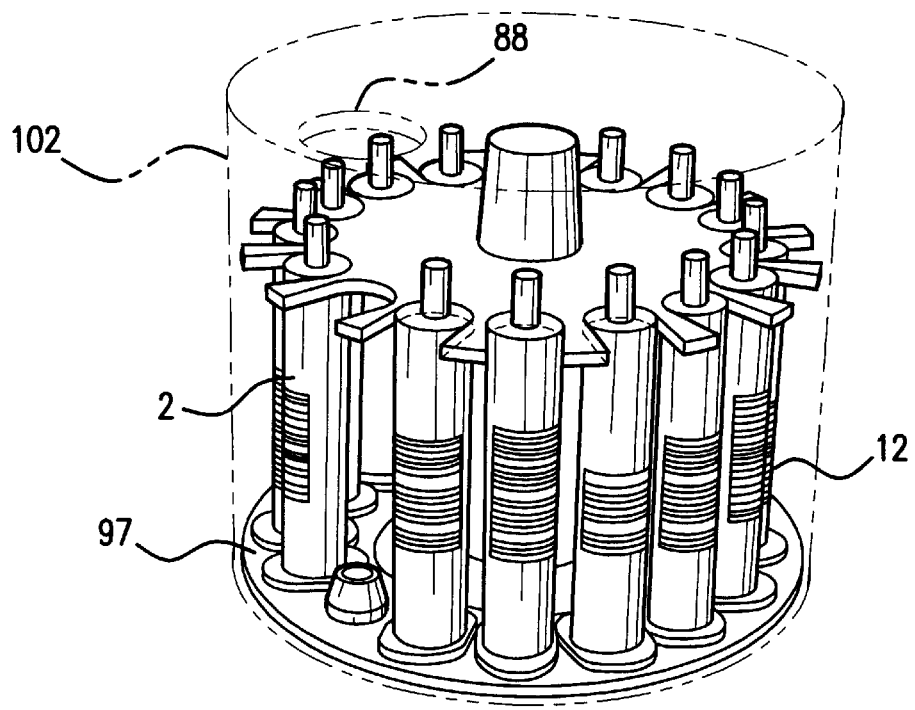
FIG. 4 illustrates an alternative cartridge storage system.

FIG. 4 shows a further embodiment of the cartridge storage system, where the cartridges 2 are mounted on a rotatable carousel 97 inside a housing 102 until needed. The carousel 97 might be actively driven or controlled by the controller in order to present only unused cartridges to the operator by way of an access point 98 in a preselected order. This embodiment provides good protection against adverse conditions.

Figure 5:
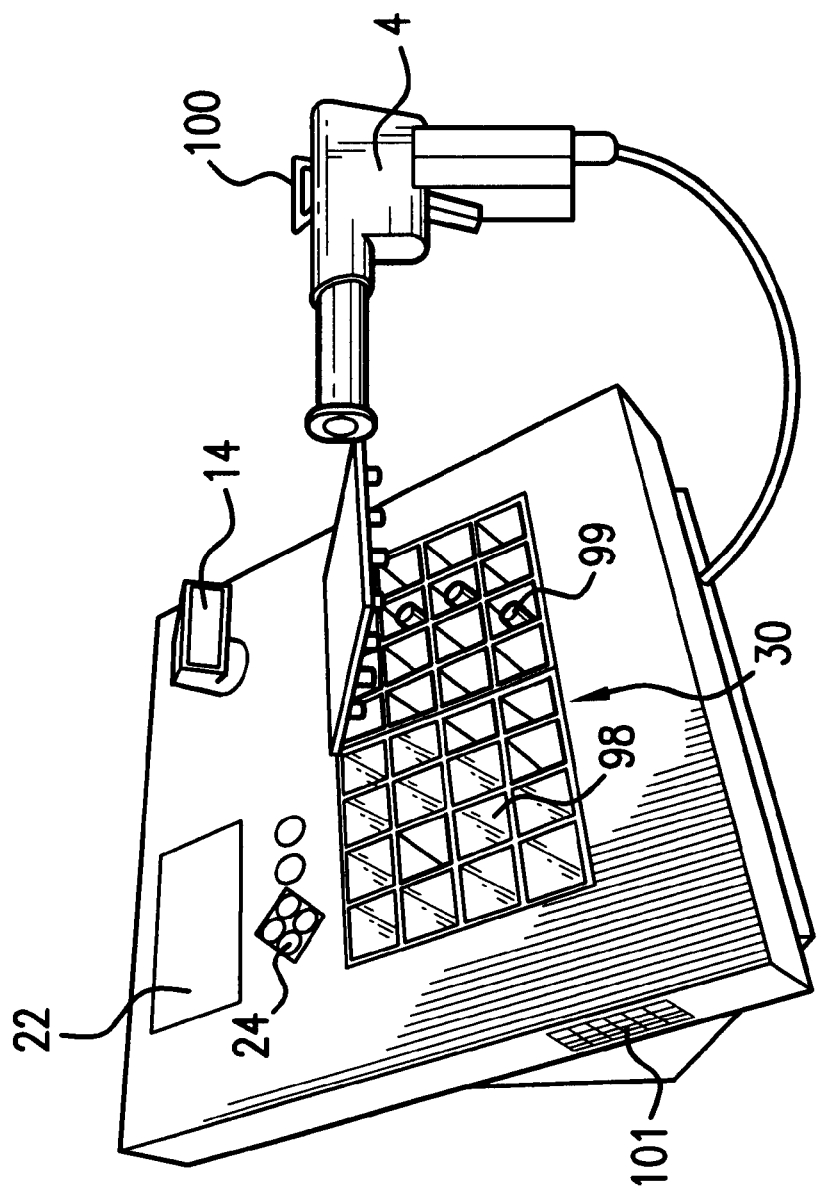
FIG. 5 is a concept drawing of elements of the system of FIG. 1.

FIG. 5 shows a concept drawing of the overall system as shown diagrammatically in FIG. 1. In this case, storage box 30 with spaces for unused cartridges 98 and used cartridges 99 is shown detachably mounted on the controller unit which includes an integral display device 22 and input device 24. The pistol grip 4 is also attached by way of a cable. A clip 100 is provided to allow mounting of the pistol grip 4 on the body of the apparatus and also to allow it to be clipped to the side of the disposable cup when taking a sample. The barcode reader 14 is detachably mounted on the body of the apparatus. An air drier 101 for removing excess liquid from the outside of the used cartridges is also included.

Once sampling is complete, or when all the SPE cartridges have been used, the storage box 30 is then removed from the controller unit and can be transported immediately to the laboratory for elution and analysis of the cartridges. The storage box is preferably made from lightweight plastic to minimise transportation costs.

Other arrangements and embodiments of the apparatus of the invention could be envisaged without departing from the invention.

What is claimed is:

1. Apparatus for sampling a liquid, said apparatus comprising:
   i) a sampling device capable of automatically taking a known volume of liquid from a source;
   ii) fixing means connected to said sampling device and removably attachable to a solid phase extraction (SPE) unit, the fixing means being arranged such that liquid taken from a sample by the sampling device is passed directly through the solid phase extraction unit;
   iii) a reading device able to read labels on an SPE unit attached to said fixing means; and
   iv) a controller arranged to log codes based upon a signal from the reading device, and thereafter issue instructions to an operator and/or operate the sampling device to take an appropriate volume of liquid in response to a signal from said reading device.

2. Apparatus according to claim 1 wherein the operation of the sampling device is monitored and the data is recorded in conjunction with information relating to the SPE unit.

3. Apparatus according to claim 1 which further comprises an input device to allow an operator to introduce data into the controller manually.

4. Apparatus according to claim 1 which further comprises interlock means which inhibit operation of the sampling device unless the controller has received an appropriate signal from the reader.

5. Apparatus according to claim 1 wherein the sampling device comprises a vessel of known volume, said vessel comprising a chamber, an inlet to allow liquid to enter said chamber, characterised in that at least a portion of a surface of the chamber comprises a gas permeable membrane, and said portion is arranged such that gas bubbles present in said chamber will exit through said membrane.

6. Apparatus according to claim 1 which further comprises a container for said SPE units.

7. Apparatus according to claim 6 wherein the container is under the command of the controller so as to control release of units contained therein.

8. Apparatus according to claim 6 wherein the container includes means for isolating at least some SPE units contained therein.

9. Apparatus according to claim 8 wherein the container has unused SPE units therein covered by a sealing film.

10. Apparatus according to claim 8 wherein the fixing means is adapted to rupture said film during an operation to obtain an SPE unit.

11. Apparatus according to claim 8 wherein a lid of the container is provided with detachable sealing means, arranged such that when the lid of the box is closed, the sealing means engage with any used SPE units present and seal them.

12. Apparatus according to claim 11 wherein the detachable sealing means comprises a Luer cap or a bung.

13. Apparatus according to claim 6 wherein sealing means are provided on the base of the container and arranged to receive and seal an inlet end of an SPE unit.

14. A method of sampling a liquid, using apparatus as claimed in claim 1 said method comprising:
   i) fitting a SPE unit having a machine readable label thereon, to the fixing means of said apparatus;
   ii) reading the label on said unit using a reading device which signals a controller with label information;
   iii) placing an inlet of said unit into a source of sample liquid; and
   iv) carrying out any instructions issued by the controller so as to cause activation of the sampling device.

15. A method according to claim 14 wherein the liquid is subject to analysis.

* * * * *